(12) United States Patent
Hell et al.

(10) Patent No.: US 8,039,815 B2
(45) Date of Patent: Oct. 18, 2011

(54) FLUORESCENT LIGHT MICROSCOPE FOR MEASURING A SAMPLE USING RED-SHIFTED STOKES LINES

(75) Inventors: Stefan W. Hell, Göttingen (DE); Brian Rankin, Göttingen (DE); Robert Kellner, Siegsdorf (DE); Jaydev Jethwa, Göttingen (DE); Thorsten Staudt, Neckargemünd (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 12/753,349

(22) Filed: Apr. 2, 2010

(65) Prior Publication Data

US 2010/0187438 A1 Jul. 29, 2010

Related U.S. Application Data

(63) Continuation of application No. PCT/EP2008/063171, filed on Oct. 1, 2008.

(30) Foreign Application Priority Data

Oct. 5, 2007 (DE) .......................... 10 2007 048 135

(51) Int. Cl.
*G01N 21/64* (2006.01)
(52) U.S. Cl. .................................... 250/458.1
(58) Field of Classification Search ............... 250/458.1, 250/459.1, 461.1, 461.2
See application file for complete search history.

(56) References Cited

U.S. PATENT DOCUMENTS 5,491,344 A * 2/1996 Kenny et al. ............... 250/461.1

6,710,918 B2 3/2004 Birk et al.
(Continued)

FOREIGN PATENT DOCUMENTS

DE 100 12 881 A1 9/2001
(Continued)

OTHER PUBLICATIONS

Benabid F et al: "Ultrahigh efficiency laser wavelength conversion in a gas-filled hollow core photonic Crystal fibre by pure stimulated rotational Raman scattering in molecular hydrogen" Physical Review Letters APS USA, vol. 93, No. 12, Sep. 17, 2004, pp. 123903/1-4.

(Continued)

*Primary Examiner* — Constantine Hannaher
(74) *Attorney, Agent, or Firm* — Thomas, Kayden, Horstemeyer & Risley LLP

(57) ABSTRACT

A fluorescent light microscope for measuring a sample comprises a light source providing transfer light having a transfer wavelength for transferring a fluorescent dye in the sample from one state into another state, and a detector which measures fluorescent light from the sample with spatial resolution. The light source comprises a laser, an optical wave guide connected to the laser, and a wavelength-selective device connected to the optical wave guide. The laser emits pump light of a pump wavelength other than the transfer wavelength and injects the pump light into the optical wave guide. The pump light, due to Raman scattering being stimulated in the optical wave guide, generates a light spectrum emerging from the optical wave guide which has, besides the pump wavelength, at least one red-shifted Stokes line whose full width at half maximum is smaller than half of its distance to its next neighbor line on the blue side of the spectrum; and the wavelength-selective device singles out the transfer light by its transfer wavelength from the red-shifted Stokes lines of the light spectrum.

27 Claims, 2 Drawing Sheets

U.S. PATENT DOCUMENTS

Figure 1:
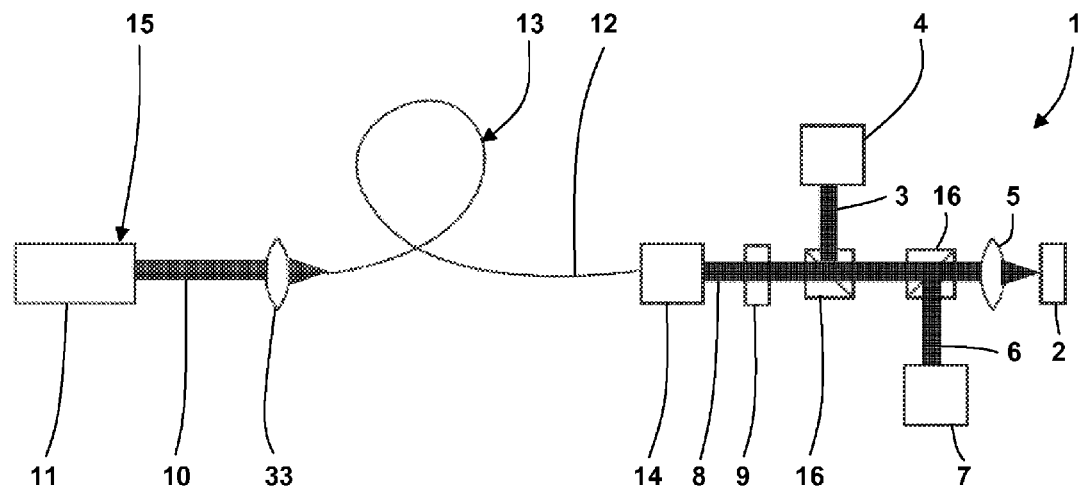

| | | | | |
|---|---|---|---|---|
| 6,813,429 B2* | 11/2004 | Price et al. | | 385/125 |
| 6,870,663 B2* | 3/2005 | Kato et al. | | 359/326 |
| 6,870,980 B2 | 3/2005 | Cremer | | |
| 7,064,824 B2* | 6/2006 | Hell | | 356/317 |
| 7,224,518 B2 | 5/2007 | Tauser et al. | | |
| 7,318,907 B2 | 1/2008 | Stark et al. | | |
| 7,433,119 B2 | 10/2008 | Gugel | | |
| 2003/0011765 A1 | 1/2003 | Xie et al. | | |
| 2005/0238070 A1 | 10/2005 | Imeshev et al. | | |
| 2006/0176542 A1 | 8/2006 | Muro et al. | | |
| 2010/0098117 A1 | 4/2010 | Fermann et al. | | |

FOREIGN PATENT DOCUMENTS

| | | |
|---|---|---|
| DE | 101 24 983 A1 | 3/2002 |
| DE | 103 47 712 A1 | 5/2005 |
| DE | 10 2005 020 003 A1 | 11/2006 |
| EP | 1 118 904 A1 | 7/2001 |
| EP | 1 288 705 A2 | 3/2003 |
| EP | 1 662 296 A1 | 3/2005 |
| WO | 03 016781 A2 | 2/2003 |
| WO | 2004 077142 A1 | 9/2004 |
| WO | 2006 114247 A1 | 11/2006 |

OTHER PUBLICATIONS

Benabid F et al: "Stimulated Raman scattering in hydrogen-filled hollow-core photonic crystal fibre" Science American Assoc. Adv. Sci USA, vol. 298, No. 5592, Oct. 11, 2002, pp. 399-402.

Benabid F et al: "Compact, stable and efficient all-fibre gas cells using hollow-core photonic crystal fibres" Nature, Nature Publishing Group, London, UK, vol. 434, No. 7032, Mar. 24, 2005, pp. 488-491.

Bewersdorf J et al: "Picosecond pulsed two-photon imaging with repetition rates of 200 and 400 Mhz" Journal of Microscopy Blackwell Science for R. Microsc. Soc UK, vol. 191, Jul. 1, 1998, pp. 28-38.

Mussot A et al: "Generation of a broadband single-mode supercontinuum in a conventional dispersion-shifted fibre by use of a subnanosecond microship laser" Optics Letters Opt. Soc. America USA, vol. 28, No. 19, Nov. 1, 2003, pp. 1820-1822.

Garzón R J et al: "Chromatic confocal microscopy by means of continuum light generated through a standard single-mode fibre" Journal of Optics, A, Pure and Applied Optics, Institute of Physics Publishing, Bristol, GB, vol. 6, No. 6, Jun. 1, 2004, pp. 544-548.

English Translation of International Search Report of co-pending, related PCT Application No. PCT/EP2008/063171, issued May 11, 2010.

* cited by examiner

FLUORESCENT LIGHT MICROSCOPE FOR MEASURING A SAMPLE USING RED-SHIFTED STOKES LINES

CROSS REFERENCE TO RELATED APPLICATIONS

This application is a continuation to International Application PCT/EP2008/063171 entitled "Fluorescent light microscopic measurement of a sample using red-shifted Stokes lines" with an International Filing Date of Oct. 1, 2008 and claiming priority to co-pending German Patent Application No. 10 2007 048 135.9 entitled "Fluoreszenzlichtmikroskopisches Messen einer Probe mit rotverschobenen Stokes-Linien", filed on Oct. 5, 2007.

FIELD OF THE INVENTION

The present invention relates to a fluorescent light microscope for measuring a sample, wherein a fluorescent dye in the sample is transferred from one state into another state with transfer light of a transfer wavelength, and wherein fluorescent light from the sample is measured with spatial resolution. More particularly, the present invention relates to a fluorescent light microscope for measuring a sample, wherein light of a pump wavelength is injected into a optical wave guide at such a minimum intensity that a light spectrum emerging from the optical wave guide, due a non-linear effect, comprises wavelengths shifted with regard to the pump wavelength, and wherein the transfer light for transferring the fluorescent dye is singled out from the spectrum by its transfer wavelength.

The intended transfer of the fluorescent dye in the sample from its one state into its other state may particularly be a transfer in any direction between a ground state and an excited state from which the fluorescent dye spontaneously emits fluorescent light, or in any direction between a fluorescent state and a dark state.

BACKGROUND OF THE INVENTION

In fluorescence microscopy, light of different wavelengths is needed (i) for exciting various fluorescent dyes for fluorescence, (ii) for purposefully de-exciting various fluorescent dyes again (for example in STED fluorescent light microscopy), (iii) for purposefully transferring various fluorescent dyes into a dark state (for example in GSD fluorescent light microscopy), or (iv), within overlapping but different spatial areas, for exciting a dye for fluorescence, on the one hand, and for de-exciting the same dye by stimulated emission or for transferring the same dye into a dark state, on the other hand. To meet these demands, a plurality of different monochromatic light sources may be used, each of which provides monochromatic light of one of the various wavelengths. As the monochromatic light sources suitable to this end are, as a rule, lasers of high quality, because the light is needed in pulses of high intensity, fluorescent light microscopes designed in this way are very expensive. For some wavelengths, it is even difficult to find suitable lasers of sufficient quality.

Inter alia from German Patent Application published as DE 10 2005 020 003 A1 and from corresponding International Patent Application published as WO 2006/114247 A1 is known to use a gas laser as a light source in fluorescent light microscopy, which displays a plurality of useable emission lines or which is at least tunable to a plurality of emission lines. Gas lasers, however, are expensive to purchase and costly in operation. In addition, in a gas laser, the suitable emission lines at best cover a small spectral range in such a way that the absorption lines of potential fluorescent dyes falling within this spectral range may be addressed at a high effective cross-section.

In a fluorescent light microscope which is known from U.S. Pat. No. 6,710,918, light of a certain wavelength used for transferring a fluorescent dye in a sample from one state into another state is provided by injecting light of another wavelength from a laser, particularly a mode-coupled titanium sapphire laser which emits at a wavelength of 800 nm, into an optical element which distributes the intensity of the injected light of one wavelength over a continuous spectrum which comprises shorter and longer wavelengths than the injected light and which is referred to as a supercontinuum. Here, the optical element may, for example, be an optical wave guide fiber strongly tapering in cross-section over a length of about 30 mm to 90 mm (a so-called "tapered fiber"), which has an overall length of about 1 m, or a micro-structured optical fiber with a photonic band gap, which is also referred to as a photonic crystal fiber. In a photonic crystal fiber, the photonic band gap is produced by a honeycomb-like microstructure around a very small fiber core of just about 2 μm diameter. The typical length of a photonic crystal fiber (PCF) is 38 cm. The continuous spectral distribution allows for selecting light of any wavelength for transferring a fluorescent dye from one state into another from the supercontinuum. The light power available at each single wavelength of the supercontinuum, however, is extremely reduced as compared to the output power of the pumping laser. Further, considerable efforts are to be taken to provide a supercontinuum having an at least approximately homogenous intensity distribution and, particularly, an intensity distribution which is stable in time. Thus, the development of corresponding fluorescent light microscopes from the patent application of this idea up to commercial products has taken more than five years. Further, the corresponding fluorescent light microscopes are expensive which is inter alia due to the titanium sapphire laser having the required output power and the PCF used in the commercial product.

In a light source for fluorescent light microscopy, including STED microscopy, which is known from German Patent Application published as DE 103 47 712 A1 and from corresponding U.S. Pat. No. 7,433,119, the wavelength of light is controlled by means of a photonic fiber or an opto-parametric oscillator (OPO). In an OPO the desired wavelength is generated by means of an optical non-linear three-wave frequency conversion process in which the input frequency of a pump wave is divided into two frequencies (signal and idler).

In a Raman amplifier arrangement on the basis of a standard single-mode fiber which is known from German Patent Application published as DE 100 12 881 A1 and from corresponding U.S. Pat. No. 6,870,980, Stokes waves are generated by means of stimulated Raman scattering of a high power optical pump signal to amplify an incoming optical signal.

A device by which incoming light is spectrally split-up based on dispersion and polarization effects is described in European Patent Application published as EP 1 662 296 A1 in corresponding US Patent Application published as US 2006176542 A1. This device is also proposed as a light source for use in STED microscopy, wherein light of a wavelength, which exactly corresponds to the wavelength of the fluorescent light of interest from a sample so that this light is particularly well suited for de-exciting by means of stimulated emission, is separated from the incoming laser beam, whereas the remaining light of the laser beam is used excitation light.

A device for generating light in a desired wavelength range, by which the excitation of a sample shall be possible in an even smaller spatial area than in STED microscopy, is known from International Patent Application published as WO 03/016781 A2 and corresponding U.S. Pat. No. 7,318, 907. Here, the light emission of the device is based on photo-induced excitation of surface plasmons in a metal layer.

There still is a need for a fluorescent light microscope for measuring a sample, in which light of different wavelengths is available to transfer various fluorescent dyes from one state into another state without high and costly efforts and without stability problems.

SUMMARY OF THE INVENTION

In an aspect, the present invention provides a fluorescent light microscope for measuring a sample, the fluorescent light microscope comprising: a light source providing transfer light having at least one transfer wavelength for transferring a fluorescent dye in a sample to be measured from one state into another state, the light source comprising a laser, an optical wave guide connected to the laser, and a wavelength-selective device connected to the optical wave guide, the laser emitting pump light of a pump wavelength other than the transfer wavelength and injecting the pump light into the optical wave guide, the pump light, due to a non-linear effect in the optical wave guide, generating a light spectrum emerging from the optical wave guide, and the wavelength-selective device singling out the transfer light by its transfer wavelength from the light spectrum emerging from the optical wave guide, wherein the optical wave guide is selected in such a way and the laser injects the pump light into the optical wave guide at such an intensity that Raman scattering is stimulated in the optical wave guide at such an extent that the light spectrum emerging from the optical wave guide, besides the pump wavelength, comprises at least one red-shifted Stokes line whose full width at half maximum is smaller than half of its distance to its next neighbour line on the blue side of the spectrum, and wherein the wavelength selective device singles out the transfer light from the red-shifted Stokes lines of the light spectrum; and a detector which measures fluorescent light from the sample with spatial resolution.

In a further aspect, the present invention provides a fluorescent light microscope for measuring a sample, the fluorescent light microscope comprising: a light source providing transfer light having at least one transfer wavelength for transferring a fluorescent dye in a sample to be measured from one state into another state, the light source comprising a laser, an optical wave guide connected to the laser, and a wavelength-selective device connected to the optical wave guide, the optical wave guide comprising a single-mode fiber having a cut off wavelength which is on the blue side of the pump wavelength, being free of microstructure and taper, and having a length of at least about 30 m, the laser emitting pump light of a pump wavelength other than the transfer wavelength, in pulses of at least about 150 watt peak power, and injecting the pulses of the pump light into the optical wave guide, the pulses of the pump light, due Raman scattering being stimulated in the optical wave guide, generating a light spectrum which emerges from the optical wave guide and which comprises at least 5 red-shifted Stokes lines whose full width at half maximum is smaller than half of their distance to their respective next neighbor line on the blue side of the spectrum, and the wavelength-selective device singling out the transfer light by its transfer wavelength from the red-shifted Stokes lines of the light spectrum; and a detector which measures fluorescent light from the sample with spatial resolution.

Other features and advantages of the present invention will become apparent to one with skill in the art upon examination of the following drawings and the detailed description. It is intended that all such additional features and advantages be included herein within the scope of the present invention, as defined by the claims.

SHORT DESCRIPTION OF THE DRAWINGS

The invention will be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 1 schematically depicts the construction of a first embodiment of the fluorescent light microscope according to the present invention.

Figure 2:
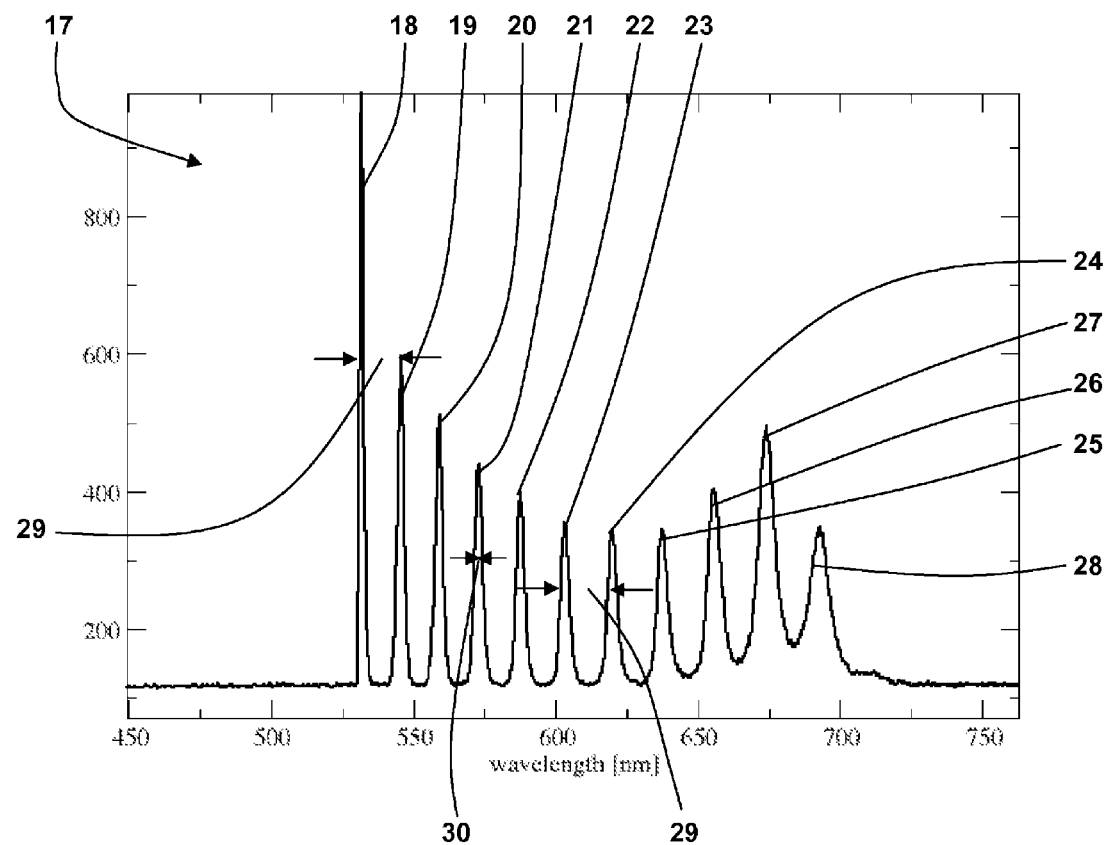

FIG. 2 is a light spectrum which is generated in the fluorescent light microscope according to FIG. 1.

Figure 3:
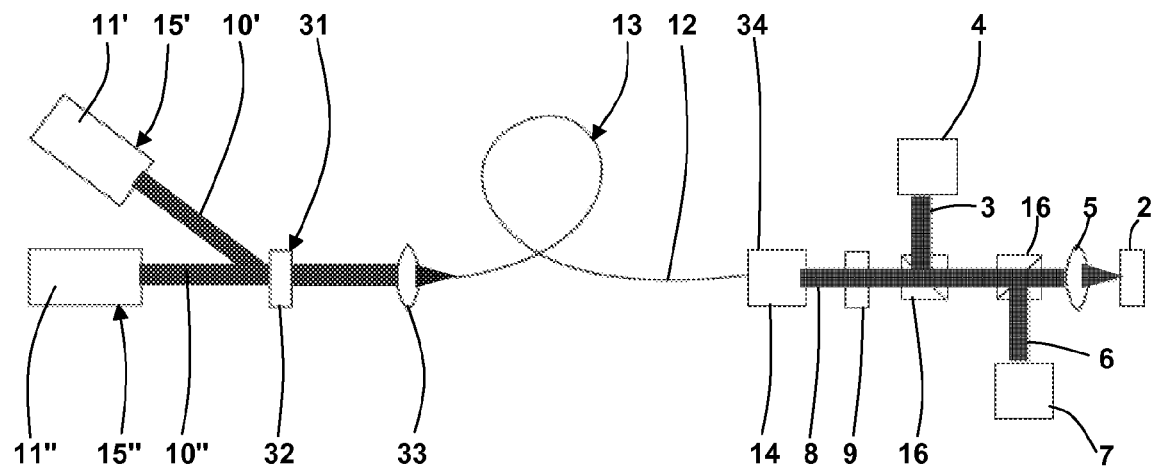
Figure 4:
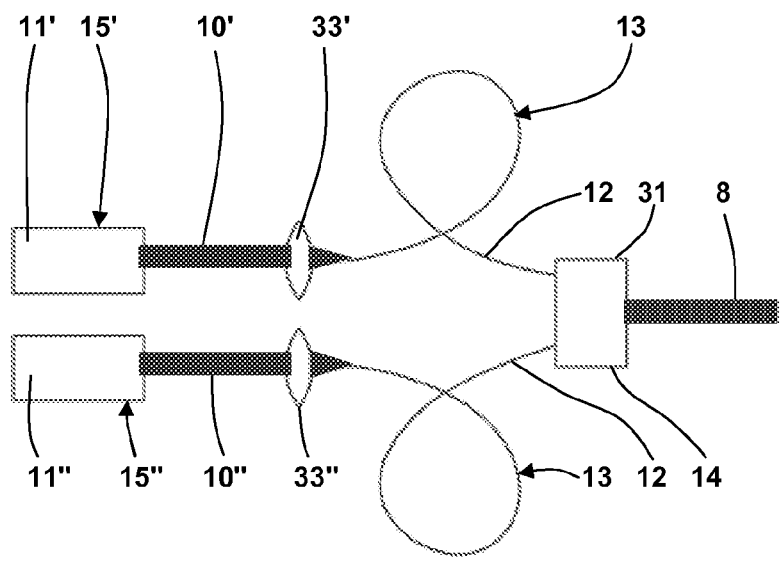

FIG. 3 schematically depicts a another embodiment of the fluorescent light microscope according to the present invention; and FIG. 4 depicts those parts of a further embodiment of the fluorescent light microscope according to the present invention which are essential for illustrating its differences to the embodiment of FIG. 3.

DETAILED DESCRIPTION

In the new fluorescent light microscope, the optical wave guide is selected in such a way and the pump light is coupled into the optical wave guide at such an intensity that Raman scattering is stimulated in the optical wave guide at such an extent that the light spectrum comprises at least one red-shifted Stokes line beside the line of the pump wavelength, the full width at half maximum of the intensity of the at least one red-shifted Stokes line being smaller than half of its distance to the line of the light spectrum which is its neighbor on the blue side; and the transfer wavelength for transferring the fluorescent dye is selected from one of the red-shifted Stokes lines.

In the new fluorescent light microscope, the effect of stimulated Raman scattering in a optical wave guide is used, which results in the formation of red-shifted Stokes lines beside the line of the injected pump light if the intensity of the injected pump light is appropriately tuned to the length of the optical wave guide. In the new fluorescent light microscope, at least one such Stokes line is generated, wherein the number of Stokes lines increases with increasing intensity of the injected pump light and with increasing length of the optical wave guide. Those Stokes lines which have the longest wavelengths, i.e. those Stokes lines red-shifted to the largest extent, are less sharply bounded. However, even that Stokes line shifted to the largest extent still displays such a small full width at half maximum that it comprises a high percentage of the intensity of the injected pump light over a small wavelength area of a few nanometers. The further Stokes lines which lie between this Stokes line red-shifted to the largest extent and the line of the injected pump light are more sharply bounded. Each of them easily fulfills the above stated criteria with regard to its full width at half maximum, and over a band of a few nanometers some percent of the intensity of the injected pump light are available. The distance between the red-shifted Stokes lines and to the line of the injected pump light is about 10-20 nm, typically about 12-15 nm, if the wavelength of the injected light is about 500 nm. The exact value of the distance depends on the material and the construction of the optical wave guide as well as on the wavelength of the injected pump light. Thus, the Stokes lines are so close that each fluorescent dye whose relevant absorption line for the desired transfer is between the wavelength of the injected light and the wavelength of the Stokes line red-shifted to the largest extent may be served with one or even some of the Stokes lines. To this end, a large portion of the intensity of the injected light is stably available over a small wavelength range within the full width at half maximum of the Stokes lines, both the position and the intensity portion of the light spectrum of the Stokes lines being stable without the need to take special measures. Advantages of the new fluorescent light microscope, however, are not only present, if there are several Stokes lines in the light spectrum emerging from the optical wave guide. Already with a single Stokes line besides the line of the injected pump light, the application possibilities of light from the emerging light spectrum are doubled.

In principle, it has already been known that red-shifted Stokes lines at uniform distances may be generated by stimulated Raman scattering in a single-mode fiber. An overview over the effects of stimulated Raman scattering will, for example, be found in Agrawal, Ch. 8: Stimulated Raman Scattering (Agrawal, Govind P., Nonlinear Fiber Optics, 2. ed., San Diego, Calif., 1995).

Despite the fact that this effect has been known for several decades, up to now no applications in the field of fluorescent light microscopy have been made. Instead, fluorescent light microscopes in which a supercontinuum is generated have been developed with high efforts, as reported at the beginning.

Even Arnaud Mussot et al.: Generation of a broadband single-mode supercontinuum in a conventional dispersion-shifted fiber by use of a subnanosecond microchiplaser (Optics Letters, Vol. 28, 0.19, Oct. 1, 2003), despite the fact that they, with increasing intensity of the injected pump light, first observed Stokes lines before the formation of a supercontinuum, only propose to make use of the supercontinuum in microscopy.

With regard to the supercontinuum prior art, however, the new fluorescent light microscope has essential advantages in that, at the wavelength of each Stokes line, it provides a much higher light intensity. On the other hand, the absence of light with wavelengths between the individual Stokes lines or between the first Stokes line and the line of the injected light is without greater relevance, as the lines are sufficiently close to each other. Further, the spectral position of the Stokes lines and their relative intensity are stable. Retrospectively, it may be surprising that the known effect of stimulated Raman scattering has been completely neglected in the development of light sources providing several wavelengths for fluorescent light microscopy.

Further, in the new fluorescent light microscope, the optical wave guide does not need to be an expensive micro-structured or locally tapering fiber. Instead, it is preferably a common single-mode fiber having an essentially constant diameter or at least no pronounced local taper and no microstructure around a fiber core of minimum diameter. On the other hand, a single-mode fiber used in the new fluorescent light microscope may be quite long. This particularly applies, if several or even many red-shifted Stokes lines are to be generated for providing transfer light for transferring fluorescent dyes from one state into another state over an extended spectral range. The single-mode fiber may have a cut-off wavelength which is not far away from the wavelength of the injected pump light, for example less than 70 nm, on the blue side. Such a single-mode fiber is single-mode over the full spectrum of the Stokes lines.

Particularly, the preferred minimum length of a common single-mode fiber in the new fluorescent light microscope is about 9 m. To obtain several red-shifted Stokes lines, however, a minimum length of 19 m is preferred. To the end of achieving a number of useable red-shifted Stokes lines in the order of 10, a length of the single-mode fiber of about 30 m or more is suitable. With 10 red-shifted Stokes lines the overall light spectrum at the output of the single-mode fiber, which comprises the wavelength of the injected light as a further line, covers a wavelength range of about 150 nm.

If the optical wave guide in the new fluorescent light microscope nevertheless is a micro-structured fiber, its length should be kept as short as possible, as micro-structured fiber have a high length-dependent attenuation as compared to common single-mode fibers. Further, a micro-structured fiber having a gas-filled hollow core is preferred in which the selection of the gas or its composition within the hollow core allows for influencing the red-shift, i.e. the spectral distance of the Stokes lines.

To delimit the high attenuation of a micro-structured fiber with a gas-filled hollow core, such a micro-structured fiber may be used to generate one Stokes line only, which only requires a comparatively short length of the micro-structured fiber. The light spectrum emerging from the micro-structured fiber and consisting of two lines may afterwards be injected into a common single-mode fiber to generate additional red-shifted Stokes lines from each of these lines.

The intensity of the pump light emitted by the laser and injected into the optical wave guide in pulses should be at least 50 watt peak power which will be sufficient for the formation of at least one Stokes line. To the end of generating more or even many Stokes lines, the intensity should reach 150 watt or even at least 450 watt peak power. As the injection efficiency is about 50%, the peak power of the pump light within the optical wave guide reaches about 50% of the peak power of the laser. The value of the peak power of the laser which is required with a certain optical wave guide for generating a certain number of Stokes lines also depends on the diameter of the optical wave guide. This diameter and the peak power together determine the intensity of the pump light within the optical wave guide.

Particularly advantageous conditions are adjusted if the pump light is injected into the optical wave guide in pulses having a duration of about 0.5 to 5 ns. With longer pulses, there is the danger that stimulated Brillouin scattering dominates within the optical wave guide. The effect of the formation of stable Stokes lines by means of stimulated Raman scattering also decreases with shorter pulses. In the new fluorescent light microscope, the duration of the pulses of the light emerging from the single-mode fiber approximately corresponds to the duration of the pulses of the injected pump light. Pulses of a duration of about 0.5 to 5 ns, and particularly pulses of a duration of about 1 to 3 ns, are of particular interest in transferring fluorescent dyes between two states in fluorescent light microscopy, if such transfers are to be driven up to saturation which may sometimes be the case.

As already mentioned, a light spectrum with several or even as many as possible red-shifted Stokes lines may be desired. Actually, the light spectrum in the new fluorescent light microscope may comprise at least 5, preferably at least 7 and most preferably at least 10 red-shifted Stokes lines. Even with an even higher number of red-shifted Stokes lines, each of these Stokes lines comprises an intensity portion of several percent of the intensity of the injected pump light.

In the new fluorescent light microscope, the Stokes lines are red-shifted. I.e. they comprise a longer wavelength than the pump light injected into the optical wave guide. In other words, the pump wavelength of the injected pump light should be located at the blue end of the visible spectrum. Gas lasers which emit in this range are extant. However, it is particularly advantageous if the pump wavelength is provided by means of frequency doubling of a basic laser frequency. Such frequency-doubled lasers may be constructed as non-expensive solid state lasers due to the basic laser frequency being in the range of about 1 μm. Thus, the light of the other wavelength may particularly be provided by means of a so-called microchip laser. A microchip laser is a type of a solid state laser available at low cost, which may for example be a frequency-doubled Nd:YAG-laser. While a frequency-doubled Nd:YAG-laser usually has an emission wavelength of 532 nm, there are also other microchip lasers which emit at other wavelengths in a range of about 450-600 nm, particularly in a range between about 500 and about 550 nm. In this way, the location of the single red-shifted Stokes lines may be influenced.

Considering a constant distance of the red-shifted Stokes lines of about 12-15 nm, Stokes lines at a distance of about 6-7 nm may be generated by means of two alternately used semiconductor laser whose emission wavelengths are offset by about 6-7 nm. Correspondingly, Stokes lines at a distance of about 4-5 nm over the entire wavelength range of the light spectrum may be provided at the output end of the optical wave guide with three different microchip lasers whose emission wavelength differ by about 4-5 nm.

Microchip lasers are particularly well suited for emitting pulses of a duration of about 1 to 3 ns. This is an optimum duration of the pulses for use in high resolution fluorescent light microscopy. The pulse repetition rate of a common microchip laser of about 1 to 100 KHz may be a little bit lower than desired for fluorescent light microscopy, where a pulse repetition rate in the megahertz range is preferred. A pulse repetition rate of 1 MHz, however, may also be realized in microchip lasers at sufficient peak power. A further opportunity is to split up the light pulses of the one transfer wavelength needed for transferring the respective fluorescent dye from its one state into its other state, which emerge from the optical wave guide, and to rearrange the parts of the pulses at an offset in time. The techniques required to this end are known to those skilled in the art. These techniques include spectrally dividing a single Stokes line and delaying one of the spectral parts by half of the distance of the pulses prior to reuniting the spectral parts.

A further option to increase the pulse repetition rate of the light of the transfer wavelength of interest, which has a certain wavelength tolerance bandwidth, is to inject different pump light pulses of different pump wavelengths which are not contemporaneous into the same optical wave guide or into several optical wave guides, and to use Stokes lines from the different pump light pulses as transfer light pulses for transferring the fluorescent dye from its one state into the other state. If the two different pump wavelengths at which the non-contemporaneous pump light pulses are injected into the optical wave guide have the distance of the Stokes lines, even light pulses exactly having the same transfer wavelength may be generated at an increased pulse repetition rate in this way. If the Stokes lines are, however, generated in different single-mode fibers, they have to display at least a little difference in wavelength to allow for aligning them on a same optical axis although they display a same polarization.

A pulse frequency increasing device, which merges light pulses in the new fluorescent light microscope to increase the pulse repetition rate of the light pulses of the transfer wavelength may include a dispersive optical element for executing the merger. Examples for suitable dispersive optical elements include prisms and prism arrangements. Particularly preferred, however, are acusto-optical filters which are used in a reverse direction for merging light pulses of only slightly differing wavelengths onto a common optical axis.

If, in the new fluorescent light microscope, an additional excitation light source, particularly a laser diode, which provides excitation light for the respective fluorescent dye, is to be triggered synchronously with regard to the transfer light pulses of the transfer wavelength by which the fluorescent dye is locally de-excited again, this can be effected by means of injecting non-contemporaneous pump light pulses of different wavelengths into the same optical wave guide or several optical wave guides without the need of synchronizing these non-contemporaneous pump light pulses with regard to each other, as a laser diode may be easily triggered in the high megahertz range without taking further measures. The two lasers emitting the non-contemporaneous pump light pulses of different wavelengths may thus be free-running with regard to each other.

Although an application of the present invention in STED fluorescent light microscopy has already been indicated in the last paragraph, the invention may also be used in common fluorescent light microscopy and in other techniques of fluorescent light microscopy displaying an increased spatial resolution due to transferring or switching fluorescent dyes between different states, like, for example, in GSD fluorescent light microscopy and RESOLFT fluorescent light microscopy.

A further possible application of the present invention, which is of particular interest, is Fluorescence Lifetime Imaging (FLIM), in which fluorescent lifetime images of a sample in the time space or frequency space are generated from the fluorescent light from the sample. The new fluorescent light microscope provides excitation light of different sufficiently finely graduated wavelengths to execute fluorescence lifetime imaging at various colors.

Referring now in greater detail to the drawings, the fluorescent light microscope 1 illustrated in FIG. 1 serves for fluorescent light microscopically measuring a sample 2 in which a structure of interest is marked with a fluorescent dye. In the focal range of an objective 5, the fluorescent dye is excited for fluorescence by means of excitation light 3 emitted by a laser diode 4. Fluorescent light 6 which is then spontaneously emitted by the fluorescent dye out of the focal range is detected by a detector 7 with spatial resolution, i.e. with allocation to a certain location in the sample 2. To the end of reducing the dimensions of the location in the sample 2, from which the fluorescent light 6 may originate, below the diffraction barrier, the fluorescent dye 2 in the sample is de-excited again outside a measurement point of interest due to stimulated emission by means of de-excitation light 8 at a wavelength differing from the excitation light 3. An interference pattern, which has an intensity zero point at the position of the measurement point of interest and an intensity around the zero point driving the stimulated emission of the fluorescent dye up to saturation, is formed of the de-excitation light 8 by means of a phase filter 9. The wavelength of the de-excitation light 8 is longer than the wavelength of pump light 10 emitted by a laser 15 being made as a microchip laser 11, which is injected into an optical wave guide 13 in the form of separate pump light pulses. The microchip laser 11 is a frequency-doubled laser 15, which emits in the blue range of the visible spectrum. The high light intensity in the optical wave guide 13 which is a common single-mode fiber 12 with a constant diameter over its entire length results in stimulated Raman scattering with several red-shifted Stokes lines being present in a light spectrum which emerges from the single-mode fiber 12. One of the Stokes lines is selected by means of a wavelength selective element 14 and forms the de-excitation light 8.

FIG. 2 shows the light spectrum 17 which emerges from the single-mode fiber 12 in the fluorescent light microscope 1 according to FIG. 1. Actually, this light spectrum 17 was produced by injecting pump light pulses having a pump wavelength of 532 nm (frequency-doubled Nd:YAG) and a pulse duration of 1.5 ns as well as a pulse repetition rate of 7 kHz at an average power of 20 mW and at a peak power of 1.9 kW into a standard single-mode glass fiber (Schaefter and Kirchhoff, cut-off wavelength about 470 nm, mode field diameter (core diameter) about 5 μm, numerical aperture 0.11, polarization-conserving Panda fiber) of 30 m length. The injection efficiency, i.e. the transmitted overall power was 50%. Similar spectra resulted with single-mode glass fibers from Thorlabs (cut-off wavelength 480 nm). The light spectrum 17 has a first line 18 of the pump light 10 injected into the single-mode fiber 12 at the pump wavelength of 532 nm at which the microchip laser 11 emits. A plurality of red-shifted Stokes lines 19 to 28 follows thereto, which each include some percent of the overall intensity of the light spectrum 17. The Stokes lines 26 to 28, red-shifted to the farthest extent, display an increasing full width at half maximum. However, they each still include several percent of the overall intensity of the light spectrum 17 over an area of a few nanometers. The distance 29 of the red-shifted Stokes lines 19 to 28 with regard to each other and of the first red-shifted Stokes line 19 to the line 18 each is about 12-15 nm. I.e., in the fluorescent light microscope according to FIG. 1, the de-excitation light 8 can be adjusted with regard to its wavelength in steps of 12-15 nm over the entire range of the spectrum 17. With the selected Stokes line, large parts of the intensity of the light 10 from the laser 11 are used for the de-excitation light 8, because each Stokes line has a full width at half maximum 30 which is smaller than half of the distance 29. With a common microchip laser 11 these portions are so intensive that they may even be split up and directed onto the sample 2 at an offset in time for doubling the pulse repetition rate of the pulses of the laser 11.

FIG. 3 illustrates another option to increase the pulse repetition rate of the de-excitation light 8 with regard to the pulse repetition rate of a single microchip laser 11. To this end, two microchip lasers 11' and 11" are provided here, which emit pump light 10' and 10", respectively, at different pump wavelengths. The pump light 10' and 10", respectively, from the two microchip lasers 11' and 11" is merged by means of a beam splitter 31, which may, for example, be constructed as an acusto-optical filter 32, onto an optical axis and injected into the single-mode fiber 12. The distance of the pump wavelength of the pump light 10' to the pump wavelength of the pump light 10" is about as high as the distance between the Stokes lines 19 to 28 according to FIG. 2 so that for each Stokes line in the light spectrum, which is generated by the pump light 10', a Stokes line of the same wavelength exists in the light spectrum, which is generated by the pump light 10". If the two lasers 11' and 11" then emit their pulses at different points in time, the de-excitation light 8 behind the wavelength-selective element 14, which is a small-bandwidth color filter 34, here, displays a doubled pulse repletion rate. The laser diode 4, which provides the excitation light 3, is triggered in dependence on both microchip lasers 11' and 11" which may be free-running with regard to each other, i.e. which do not need to be synchronized with regard to each other.

Whereas the fluorescent light microscope 1 according to FIG. 3 only uses one single-mode fiber 12 in increasing the pulse repetition rate of the de-excitation light 8, two single-mode fibers 12' and 12", each of which receives the pump light 10' or 10" from one of the microchip lasers 11' or 11" and forms one light spectrum with Stokes lines, are used according to FIG. 4. Here, the two light spectra are merged by means of a beam splitter 31 which also is the wavelength-selective element 14 so that two Stokes lines having slightly different wavelengths, but which may nevertheless both be used as the de-excitation light 8, are merged on the common optical axis. The part of the fluorescent light microscope according to FIG. 4 which follows the phase filter 9 is not depicted here, as it is identical to FIG. 3.

Many variations and modifications may be made to the preferred embodiments of the invention without departing substantially from the spirit and principles of the invention. All such modifications and variations are intended to be included herein within the scope of the present invention, as defined by the following claims.

We claim:

1. A fluorescent light microscope for measuring a sample, the fluorescent light microscope comprising:

a light source providing transfer light having at least one transfer wavelength for transferring a fluorescent dye in a sample to be measured from one state into another state, the light source comprising at least one pulsed laser, an optical wave guide comprising a single-mode fiber that is connected to the at least one pulsed laser, and a wavelength-selective device connected to the optical wave guide, the at least one pulsed laser emitting pump light of a pump wavelength other than the transfer wavelength and injecting the pump light into the optical wave guide as high peak power pulses, the high peak power pulses of the pump light, due to a non-linear effect in the optical wave guide, generating a light spectrum emerging from the optical wave guide, and the wavelength-selective device singling out the transfer light by its transfer wavelength from the light spectrum emerging from the optical wave guide, wherein the pulses have a duration in a range from about 0.5 to about 5 ns, wherein the optical wave guide is selected in such a way and the at least one pulsed laser injects the pump light into the optical wave guide at such an intensity that Raman scattering is stimulated in the optical wave guide at such an extent that the light spectrum emerging from the optical wave guide, besides the pump wavelength, comprises at least one red-shifted Stokes line whose full width at half maximum is smaller than half of its distance to its next neighbour line on the blue side of the spectrum, and wherein the wavelength selective device singles out the transfer light from the red-shifted Stokes lines of the light spectrum, wherein light emerging from the optical wave guide is pulsed, wherein i the light emerging from the optical wave guide have about the same duration as the duration of the pulses;

an excitation light source which provides excitation light for exciting the fluorescent dye for fluorescence, the excitation light source comprising a laser diode triggered synchronously with the at least one pulsed laser; and
a detector which measures fluorescent light from the sample with spatial resolution.

2. The fluorescent light microscope of claim 1, wherein the optical wave guide comprises a single-mode fiber having a cut off wavelength which is on the blue side of the pump wavelength.

3. The fluorescent light microscope of claim 2, wherein the single-mode fiber is free of microstructure and taper.

4. The fluorescent light microscope of claim 2, wherein the single-mode fiber has a length of at least about 9 m.

5. The fluorescent light microscope of claim 2, wherein the length of the single-mode fiber is at least about 19 m.

6. The fluorescent light microscope of claim 5, wherein the length of the single-mode fiber is at least about 30 m.

7. The fluorescent light microscope of claim 2, wherein the optical wave guide comprises a micro-structured fiber having a gas-filled hollow core, at its input side, and a single-mode fiber connected to the micro-structured fiber, at its output side.

8. The fluorescent light microscope of claim 1, wherein the optical wave guide comprises a micro-structured fiber having a gas-filled hollow core.

9. The fluorescent light microscope of claim 1, wherein the at least one pulsed laser injects the pump light into the optical wave guide in pulses of at least about 50 watt peak power.

10. The fluorescent light microscope of claim 9, wherein the at least one pulsed laser injects the pump light into the optical wave guide in pulses of at least about 150 watt peak power.

11. The fluorescent light microscope of claim 10, wherein the at least one pulsed laser injects the pump light into the optical wave guide in pulses of at least about 450 watt peak power.

12. The fluorescent light microscope of claim 9, wherein the pulses have a duration in a range from about 1 to about 3 ns.

13. The fluorescent light microscope of claim 9, wherein the light source further comprises a pulse repetition frequency increasing device which splits pulses of the transfer light emerging from the optical wave guide into partial pulses and merges them again at a relative offset in time.

14. The fluorescent light microscope of claim 13, wherein the pulse repetition frequency increasing device comprises a dispersive optical element merging the light pulses.

15. The fluorescent light microscope of claim 9, wherein the light source further comprises a pulse repetition frequency increasing device which injects different, non-contemporaneous pulses of pump light of different pump wavelengths into the optical wave guide and merges closely neighbouring Stokes lines generated by the pulses of the pump light of the different pump wavelengths as pulses of the transfer light.

16. The fluorescent light microscope of claim 15, wherein the pulse repetition frequency increasing device comprises a dispersive optical element merging the light pulses.

17. The fluorescent light microscope of claim 9, wherein the light source further comprises at least one further optical wave guide and a pulse repetition frequency increasing device which injects different, non-contemporaneous pulses of pump light of different pump wavelengths into the optical wave guides and merges closely neighbouring Stokes lines generated by the pulses of the pump light of the different pump wavelengths in the optical wave guides as pulses of the transfer light.

18. The fluorescent light microscope of claim 17, wherein the pulse repetition frequency increasing device comprises a dispersive optical element merging the light pulses.

19. The fluorescent light microscope of claim 1, wherein the light spectrum comprises at least 2 red-shifted Stokes lines.

20. The fluorescent light microscope of claim 19, wherein the light spectrum comprises at least 5 red-shifted Stokes lines.

21. The fluorescent light microscope of claim 1, wherein the light spectrum comprises at least 10 red-shifted Stokes lines.

22. The fluorescent light microscope of claim 1, wherein the at least one pulsed laser is a frequency-doubled laser.

23. The fluorescent light microscope of claim 22, wherein the at least one pulsed laser is a microchip laser.

24. The fluorescent light microscope of claim 1, wherein the at least one pulsed laser is a microchip laser.

25. The fluorescent light microscope of claim 1, wherein the at least one pulsed laser emits the pump light at the pump wavelength in a range from about 450 to about 600 nm.

26. The fluorescent light microscope of claim 1, wherein the at least one pulsed laser emits the pump light at the pump wavelength in a range from about 500 to about 550 nm.

27. A fluorescent light microscope for measuring a sample, the fluorescent light microscope comprising:
a light source providing transfer light having at least one transfer wavelength for transferring a fluorescent dye in a sample to be measured from one state into another state,
the light source comprising at least one pulsed laser, an optical wave guide connected to the at least one pulsed laser, and a wavelength-selective device connected to the optical wave guide,
the optical wave guide comprising a single-mode fiber having a cut off wavelength which is on the blue side of the pump wavelength, being free of microstructure and taper, and having a length of at least about 30 m,
the at least one pulsed laser emitting pump light of a pump wavelength other than the transfer wavelength, in pulses of at least about 150 watt peak power, a duration in a range from about 0.5 to about 5 ns, and injecting the pulses of the pump light into the optical wave guide,
the pulses of the pump light, due Raman scattering being stimulated in the optical wave guide, generating a light spectrum which emerges from the optical wave guide and which comprises at least 5 red-shifted Stokes lines whose full width at half maximum is smaller than half of their distance to their respective next neighbouring line on the blue side of the spectrum,
the wavelength-selective device singling out the transfer light by its transfer wavelength from the red-shifted Stokes lines of the light spectrum;
an excitation light source which provides excitation light for exciting the fluorescent dye for fluorescence, the excitation light source comprising a laser diode triggered synchronously with the at least one pulsed laser,
wherein light emerging from the optical wave guide is pulsed, and wherein the light emerging from the optical wave guide comprises about the same duration as the duration of the pulses; and
a detector which measures fluorescent light from the sample with spatial resolution.

* * * * *